United States Patent [19]
Klyce et al.

[11] Patent Number: 4,863,430
[45] Date of Patent: Sep. 5, 1989

[54] INTRODUCTION SET WITH FLEXIBLE TROCAR WITH CURVED CANNULA

[75] Inventors: Henry Klyce, Piedmont; Benjamin S. Clawson, Oakland, both of Calif.

[73] Assignee: Surgical Dynamics, Inc., San Leandro, Calif.

[21] Appl. No.: 89,600

[22] Filed: Aug. 26, 1987

[51] Int. Cl.⁴ .............................................. A61M 5/18
[52] U.S. Cl. ................................... 604/164; 604/170; 128/305
[58] Field of Search ................. 604/51, 52, 164–169, 604/264, 265, 280, 165, 93, 170; 128/343, 348.1, 305.1, 772, 305, 310, 311

[56] References Cited

U.S. PATENT DOCUMENTS

| | | | |
|---|---|---|---|
| 387,454 | 8/1888 | Siegenthaler | 604/164 |
| 1,248,492 | 12/1917 | Hill | 604/165 |
| 1,906,678 | 5/1933 | Wappler | 604/170 |
| 2,118,631 | 5/1938 | Wappler | 604/170 |
| 2,828,744 | 4/1958 | Hirsch et al. | 604/165 |
| 3,169,527 | 2/1965 | Sheridan | 604/265 |
| 3,521,620 | 7/1970 | Cook | 604/170 |
| 3,537,451 | 11/1970 | Murray | 604/165 |
| 3,547,103 | 12/1970 | Cook | 604/170 |
| 3,566,874 | 8/1971 | Shepherd | 604/265 |
| 3,592,192 | 7/1971 | Harautuneian | 604/165 |
| 3,948,273 | 4/1976 | Sanders | 604/280 |
| 4,143,423 | 3/1979 | Sternlieb | 604/265 |
| 4,368,730 | 1/1983 | Sharrock | 604/164 |
| 4,379,458 | 4/1983 | Bauer et al. | 604/264 |
| 4,534,363 | 8/1985 | Gold | 604/265 |
| 4,573,448 | 3/1986 | Kambin | 128/1 R |
| 4,609,370 | 9/1986 | Morrison | 604/165 |
| 4,627,844 | 12/1986 | Schmitt | 604/264 |
| 4,636,346 | 1/1987 | Gold et al. | 604/280 |
| 4,676,249 | 6/1987 | Arenas et al. | 604/164 |
| 4,732,163 | 3/1988 | Bonello et al. | 604/280 |
| 4,756,708 | 7/1988 | Martin | 604/93 |

FOREIGN PATENT DOCUMENTS

48504 4/1985 PCT Int'l Appl. ................. 128/772

*Primary Examiner*—John D. Yasko
*Attorney, Agent, or Firm*—Fliesler, Dubb, Meyer & Lovejoy

[57] ABSTRACT

An introduction set 20 is adapted for positioning a probe 22 relative to a desired site in a subject 128. The introduction set 20 includes an elongated flexible trocar 24 adapted for insertion into the subject 128 relative to the desired site. The trocar 24 has a flexible body 34 adapted to be bent out of the way of the equipment. The introduction set 20 further includes a curved cannula 26 having an elongated arcuate tubular body 60 and an elongate friction reducing tubular lining 64 disposed within the tubular body 60. The introduction set 20 further includes a dilator 28 which can be disposed in the cannula 26 for facilitating the introduction of the cannula 26 into the subject 128. The cannula 26 and dilator 28 are inserted over the trocar 24. The trocar 24 is of sufficient length such that, with the cannula 26 completely thread over the trocar 24, the trocar 24 extends from the back end 44 of the cannula 26 so that the position of the trocar 24 can be continuously monitored and maintained. The introduction set 20 further includes a seal nut 30 which can be lockingly secured to the cannula 26 with the trocar 24 and dilator 28 removed. The seal nut 30 provides a seal between the probe 22 and the cannula 26.

21 Claims, 6 Drawing Sheets

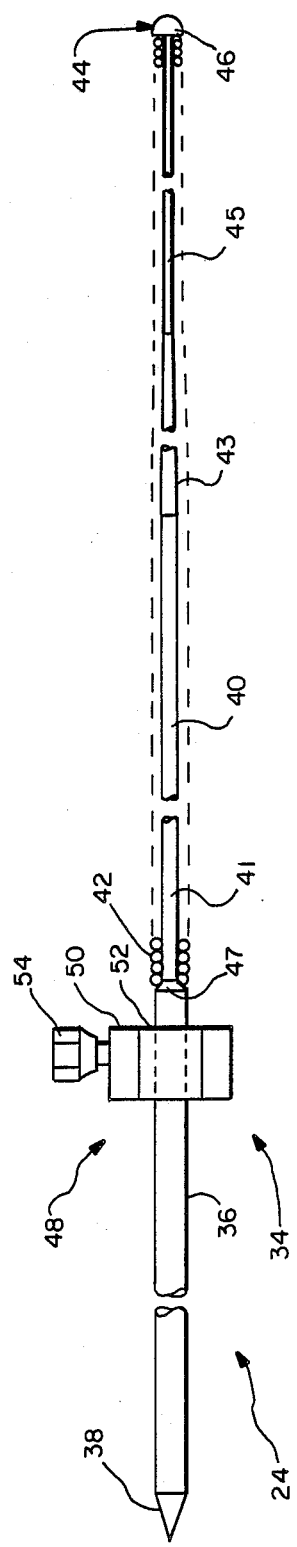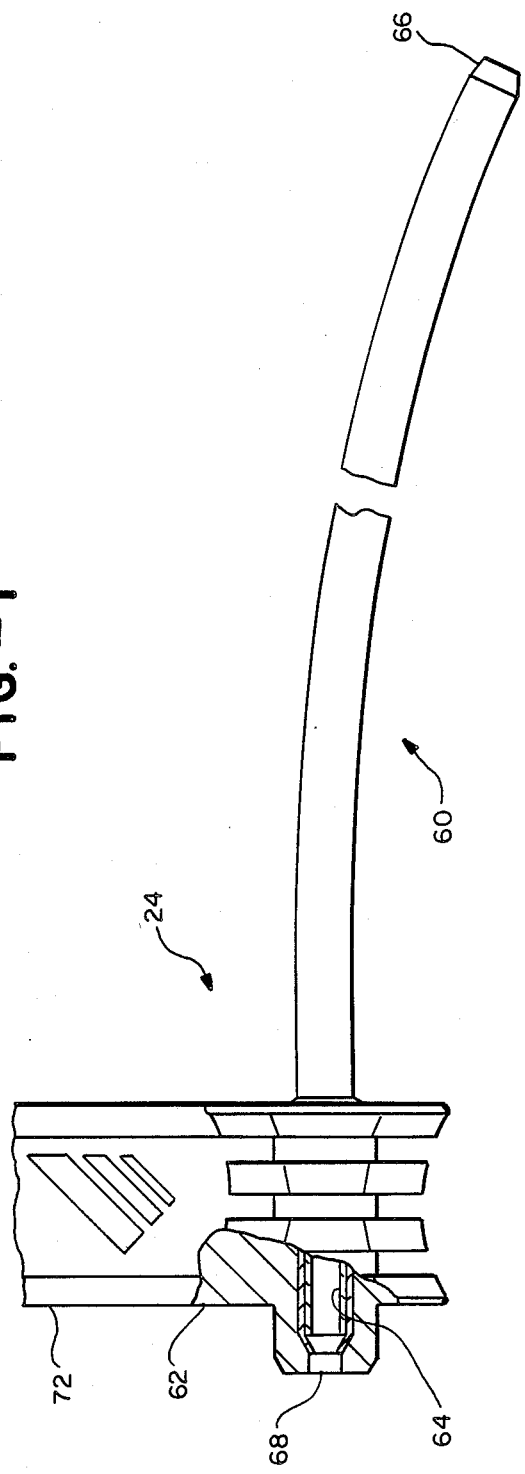

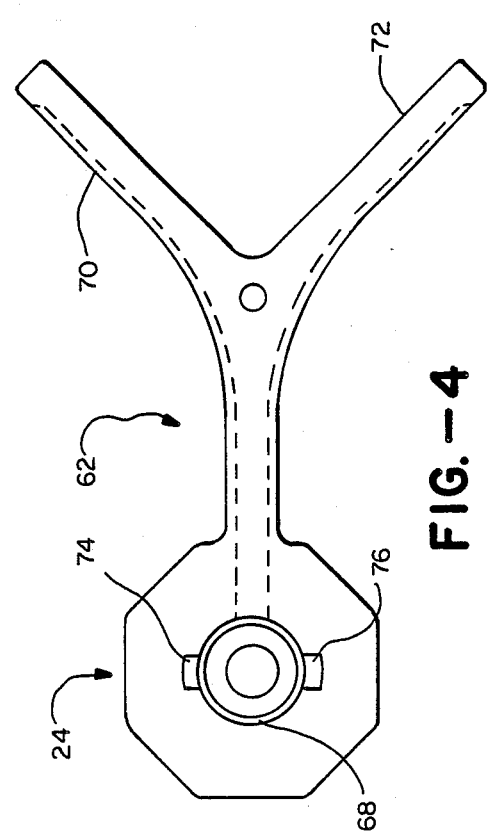
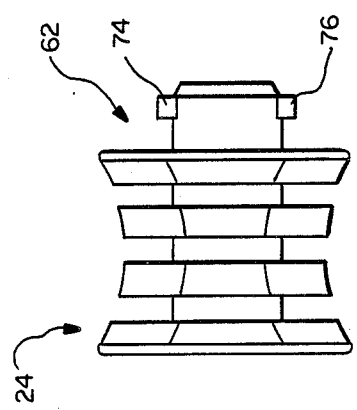
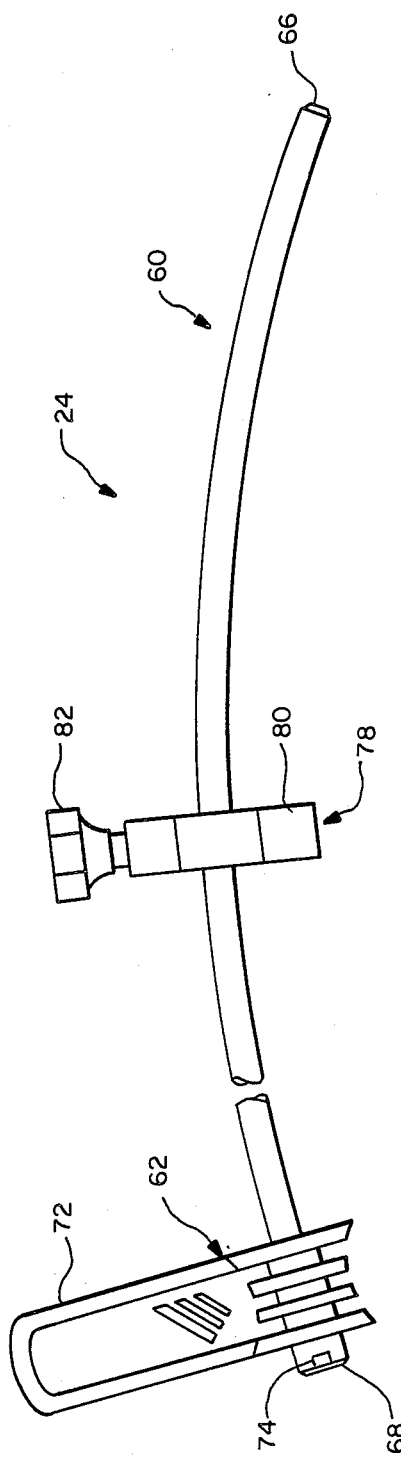

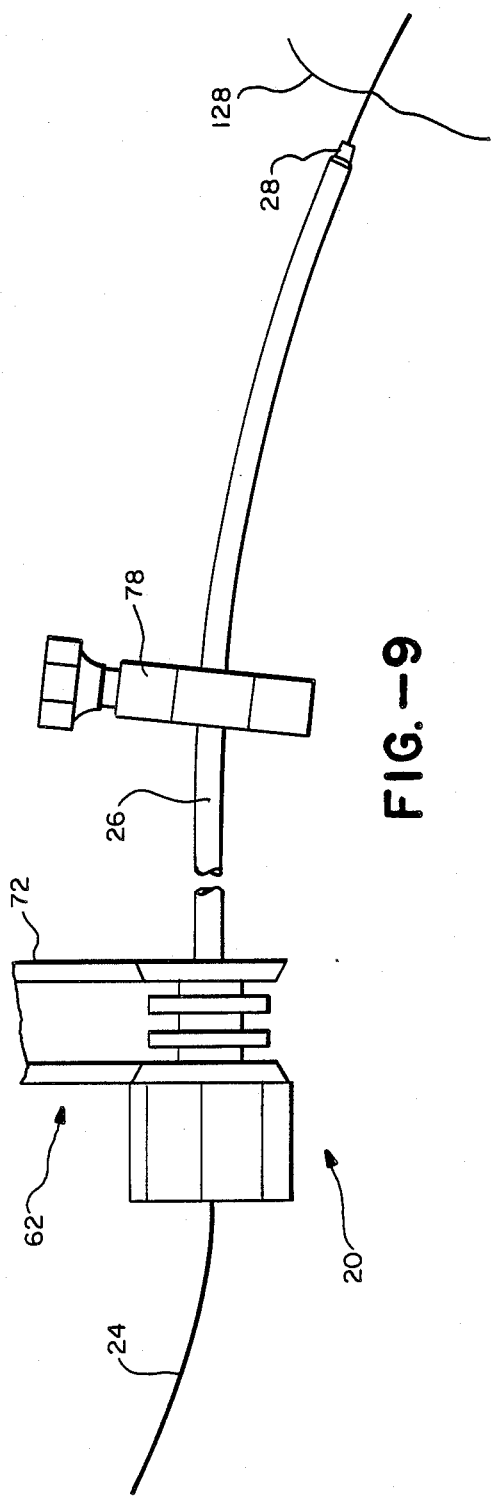
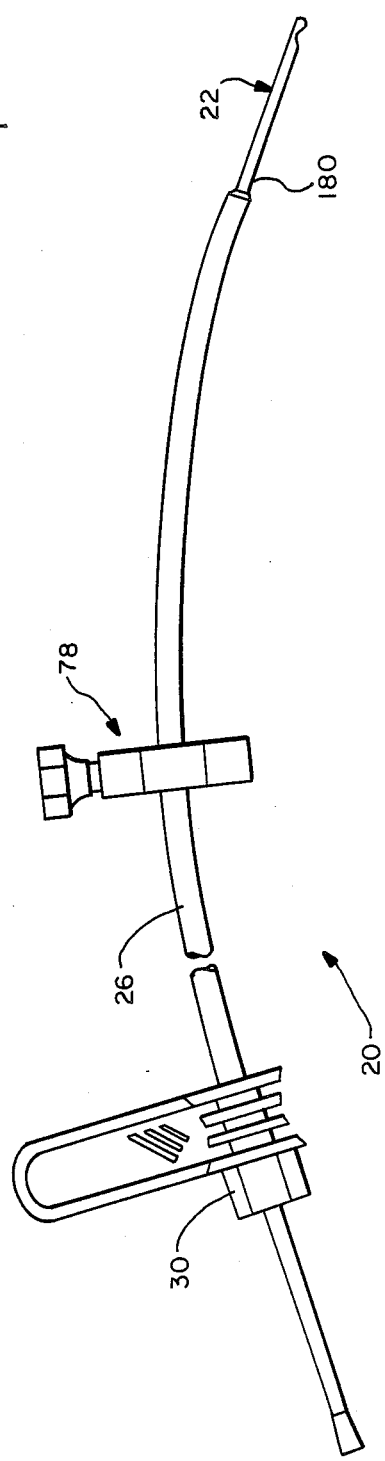
FIG.-9
FIG.-17

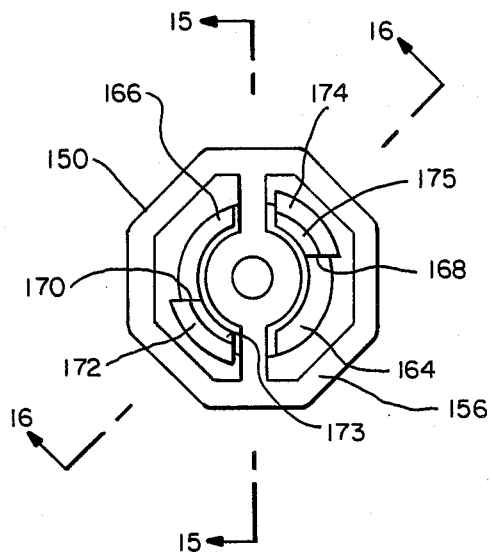
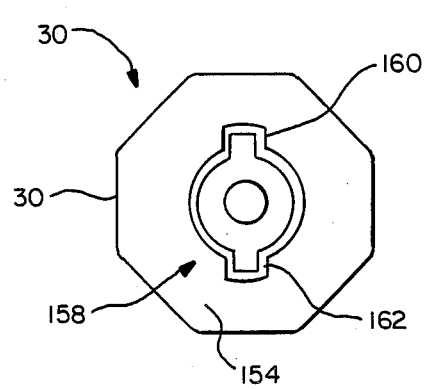
FIG.-13
FIG.-14
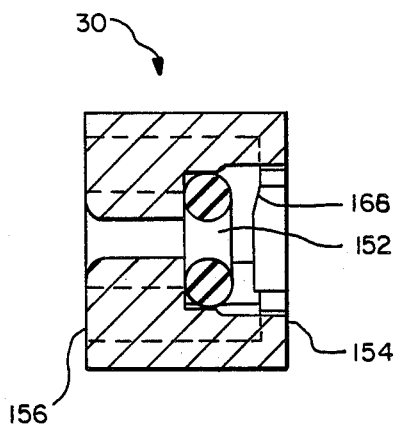
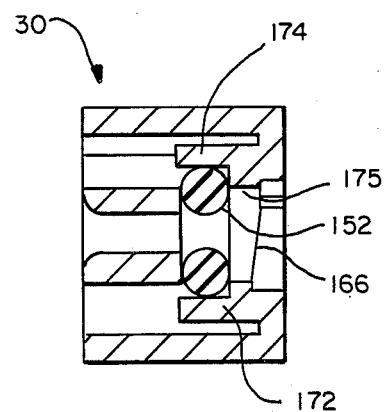
FIG.-15
FIG.-16
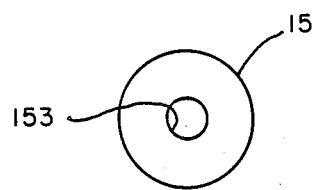
FIG.-16a

INTRODUCTION SET WITH FLEXIBLE TROCAR WITH CURVED CANNULA

FIELD OF THE INVENTION

The present invention is directed to an introduction set for the placement of both a cannula and a probe relative to a desired site in a subject.

BACKGROUND ART

Introduction sets for surgical procedures including such procedures as (1) placing a cannula adjacent a cavity to be drained, (2) introducing a diagnostic tool, and (3) introducing surgical tools, such as a biopsy probe, a trephine, or other cutting probe, are well known in the art. These introduction sets generally include a straight trocar with a sharpened end. The trocar, being generally a small diameter rigid wire, can be inserted into the subject and located adjacent the desired site. By insertion over the trocar, a combination of a dilator and a cannula can be introduced through the subject to the desired site. The cannula includes generally a straight tubular body with the dilator including a second straight tubular body which is inserted inside the tubular body of the cannula. The dilator includes a conical end which extends from the tubular body of the cannula. As the cannula and dilator pass over the trocar, the dilator expands the tissue of the subject to accommodate the larger diameter tubular body of the cannula. Once the cannula has been properly inserted, the trocar can be extracted along with the dilator in order to allow the desired procedure to be performed through the unobstructed cannula.

At times, due to the location of the desired site to be accessed in the subject, it is difficult to use a straight cannula. Thus there is a requirement for an introduction set which can accomplish other than a straight-in approach to the desired site.

SUMMARY OF THE INVENTION

The present invention is directed to overcoming the disadvantages of an introduction set with only a straight cannula.

An introduction set of the embodiment of the invention for positioning a probe relative to a desired site in a subject comprises an elongated flexible trocar adapted for insertion into a subject. The flexible trocar has an insertion end which is generally sharpened and a back end. The flexible trocar has a flexible section adapted for extension from the subject which can be flexed out of the way of adjacent equipment.

The introduction set further includes a curved cannula having an elongated arcuate tubular body and an elongate friction reducing tubular lining disposed inside the tubular body for guiding the tubular body over the flexible trocar. The curved cannula is shorter than the flexible trocar such that, with the flexible trocar extended from the subject, the tubular body of the cannula can be guided over the flexible trocar and directed toward the subject. Prior to the introduction of the cannula into the subject, the back end of the flexible trocar extends from the cannula. With this arrangement, the position of the flexible trocar can be observed as the cannula is inserted into the subject. The flexible trocar can be in fact held so that the introduction of the cannula does not further urge the trocar into the subject. A dilator can be inserted into the subject with the cannula to facilitate the introduction of the cannula over the trocar into the subject.

After the cannula is properly positioned, the dilator can be removed and a hole saw or trephine inserted over the flexible trocar. The hole saw, guided by the flexible trocar, can cut through fibrous tissue of the subject. Again the flexible trocar extends from the back of the trephine prior to the trephine being inserted into the cannula. Thus the back end of the flexible trocar can be held as the trephine is inserted so as to prevent the flexible trocar from being advanced further into the subject. The trephine has cutting teeth which are angled inwardly so as to avoid damaging the friction reducing lining located inside the cannula.

It is to be further understood that due to the length of the flexible trocar, the position of the flexible trocar can be observed and maintained as the dilator is removed from the subject.

Once the trephine and trocar are removed, a probe, such as for example one which can cut and remove tissue, can then be inserted through the curved cannula. The friction reducing tubular lining facilitates the introduction of the probe through the curved cannula to the desired site.

A seal nut with an O-ring provides a seal between the curved cannula and the probe while still allowing the movement of the probe relative to the cannula. Such a seal is important where the probe includes a tissue removal function facilitated by a vacuum procedure. The seal provides for the maintenance of the appropriate vacuum.

Accordingly, it is an object of the present invention to provide an introduction set having a curved cannula for allowing the cannula to be positioned adjacent a desired site in the subject without the need for a straight-in approach to that site.

Another object of the present invention is to provide for a flexible trocar which can guide the curved cannula to the desired site and which can be flexed out of the way of equipment such as for example, a fluoroscope or other x-ray equipment.

Yet a further object of the invention is to provide a flexible trocar which is of sufficient length such that it can extend from the cannula or the trephine prior to the insertion of the cannula or trephine into the subject so that the position of the flexible trocar can be maintained.

Yet a further object of the invention is to provide for a curved cannula with a friction reducing tubular lining which facilitates the introduction of a probe.

Yet another object of the present invention is to provide for the maintenance of a vacuum between the curved cannula and the probe.

Still a further object is to provide for a trephine which can be inserted into the cannula without damage to the friction reducing lining.

Another object of the invention is to provide for the removal of an increased amount of tissue by moving the probe in and out of the cannula and by rotating the probe inside the cannula while continuing to use the probe to cut tissue.

Yet another object of the invention is also to provide for the removal of an increased amount of tissue by rotating the curved cannula so as to allow the probe extending therethrough to access a new site in the subject.

BRIEF DESCRIPTION OF THE FIGURES

FIG. 1 is a side view of an embodiment of the flexible trocar of the invention.

FIG. 2 is a side view of an embodiment of the curved cannula of the invention.

FIG. 3 is a top view of the handle of the curved cannula of FIG. 2.

FIG. 4 is an end view of the curved cannula of FIGS. 2 and 3.

FIG. 5 is a side view of the curve cannula of the invention similar to FIG. 2 with the addition of a stop.

FIG. 9 is a side view of an assembled embodiment of the above depicted flexible trocar, curved cannula and dilator of the invention.

FIG. 13 is a bottom end view of an embodiment of the seal nut of the invention.

FIG. 14 is a top end view of the seal nut of FIG. 13.

FIG. 15 is a section view taken through line 15—15 of FIG. 13.

FIG. 16 is a section view taken through line 16—16 of FIG. 13.

FIG. 16a is a front view of an O-ring of the invention.

FIG. 17 is a side view of an assembly of an embodiment of the invention including a flexible trocar and seal nut with a probe-inserted through the curved cannula.

DETAILED DESCRIPTION OF THE PREFERRED EMBODIMENT

With reference to the figures, the present invention includes an introduction set 20 to be used in a preferred embodiment in order to introduce a probe 22 into a subject, such as a human patient. While any number and type of probes can be used with the introductory set 20 of the invention, it is highly advantageous if a probe described and claimed in U.S. Pat. No. 4,678,459 issued on July 7, 1987 and directed to an Irrigating, Cutting And Aspirating System For Percutaneous Surgery be used with the introduction set of the invention. The above referenced patent is incorporated herein by reference.

Figure 11:
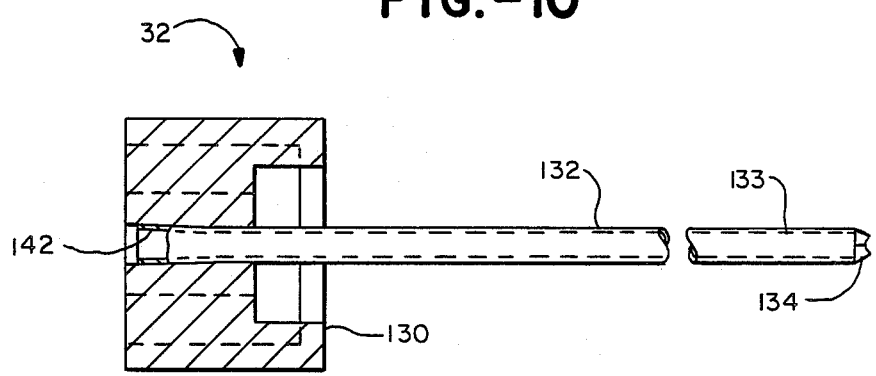
FIG. 11 is a partially sectioned side view of the trephine of FIG. 10.

Selected portions of the introduction set 20 of the invention can be seen in FIGS. 9 and 17. The portions in FIG. 9 include the flexible trocar 24, the curved cannula 26 and the dilator 28. In FIG. 17 the seal nut 30 of the introduction set 20 is also depicted. The introduction set further includes a trephine 32 with tapered teeth 134 as depicted in FIG. 11.

Starting with the flexible trocar 24, each component of the introduction set 20 is described followed by a description of the operation of all the components.

The flexible trocar 24 is shown in greater detail in FIG. 1. As can be seen in FIG. 1, the trocar 24 includes an elongated substantially flexible body 34 which has a first flexible section 36 with a sharpened insertion end 38. The body 34 further includes a second flexible section 40 which has a diameter which is substantially less than the diameter of the first portion 36. In a preferred embodiment second flexible section 40 includes a first portion 41, a tapered transition portion 43 and a second portion 45. In a preferred embodiment, the diameter of the first section 36 is about 0.051 inches while the diameter of the first portion 41 of the second section 40 is about 0.029 inches and the diameter of the second portion is 0.019. In a preferred embodiment the flexibility of the second section 40 is substantially greater than the flexibility of the first section 36 such that the second section 40 can be bent to about ninety degrees and more and returned to a substantially straight position without damage or fatigue to the trocar 24. The advantage of the trocar being flexible as described above will become apparent with the description of the introduction set 20 used in combination with for example a fluoroscope. When used with a fluoroscope, it is necessary that the trocar be flexible so as to be positionable out of the way of the fluoroscope as it swings into position to make appropriate images of the position of the trocar as positioned in a subject. It is to be understood that other embodiments of trocar that can flex less and also more than ninety degrees fall within the scope and spirit of the invention. In a preferred embodiment it is desired that, for example, the trocar flex sufficiently to allow a fluoroscope to swing by. An embodiment of a trocar which can flex back and touch itself is within the spirit and scope of the invention.

In a preferred embodiment, the first and second section 36, 40 are of one piece integral construction with material removed from the body 34 by, for example, grinding to create the reduced diameter second section 40. Also in a preferred embodiment it is to be understood that the trocar 24 is made of 304 stainless steel.

Placed about and in contact with the second flexible section 40 is a coiled wire 42 which assists in providing to the trocar 24 the desired flexibility. The coiled wire 42 in a preferred embodiment is also comprised of 304 stainless steel. The outer diameter of the coiled wire 42 is substantially that of the first flexible section 36. The coiled wire 42 is secured to the back end 44 of the trocar, in a preferred embodiment by forming a welded hemisphere 46 which secures the coiled wire 42 to the end of the second section 40. The other end of the coiled wire 42 is, in a preferred embodiment, brazed to the beveled transition section 47 between the first and second flexible sections 36, 40.

It is to be understood that the above specific embodiment can in fact be flexed further than ninety degrees and in fact can be bent back upon itself multiple times without fracturing or deforming the materials.

In a preferred embodiment the flexible trocar is approximately sixteen inches long. Thus the ratio of the trocar to the diameter of the first flexible section is on the order of about 300 to one.

It is to be understood that alternatively other embodiments of the invention are possible. By way of example only, another embodiment of the invention can include a body 34 which is composed of several individual pieces which are joined together. For example, first section 36 can be formed separately from second section 40 and the two sections joined together by for example providing a bore in section 36 to which second section 40 is inserted and then providing for the welding of the second section 40 to the first section 36. Additionally it is possible for the formation of a trocar such as trocar 24 and having a body such as body 34, without the use of the coiled wire 42.

The flexible trocar 24 further includes a handle 48 which facilitates the placement of the trocar 24 relative to the body. The handle 48 includes a body 50 having a port 52 through which the body 34 and principally the first section 36 of trocar 24 is disposed. A screw 54 is used to selectively secure the body 50 of the handle 48 to the flexible body 34 of the trocar 24.

The curved cannula 26 of the invention is depicted in greater detail in FIGS. 2, 3, 4 and 5. In FIG. 2 the curved cannula 24 includes an elongated arcuate tubular body 60 and a handle 62. The elongated arcuate tubular body 60 in a preferred embodiment is comprised of 304 stainless steel and is designed to accept a probe with an outer diameter of about two millimeters.

A tubular lining 64 comprised of a friction reducing material is disposed inside of the elongated arcuate tubular body 60 and extends from insertion end 66 of the tubular body 60 to about the back end 68 of the tubular body 60. In a preferred embodiment, the tubular lining 64 is comprised of Teflon ®. The tubular lining 64 is maintained in the elongated arcuate tubular body 60 of the curved cannula 26 by swaging ends 66 and 68 so as to reduce the diameter thereof. Other methods of securing the lining 64 in the tubular body 60 include for example molding a stop into the handle 62 to prevent the lining 64 from escaping through the back end 68 of the cannula 24.

Lining 64 assists in reducing the friction between for example a probe such as probe 22 which can be comprised of stainless steel and the cannula 26. It is to be understood that as the cannula 26 is curved, that absent the lining 64, that the stainless steel of the probe would be in direct contact with the stainless steel of the cannula causing increased friction as the cannula flex the substantially straight probe 22 in order to properly position the probe 22. When rubbing of like materials occurs, it is possible that galling can occur with the resultant wearing of the cannula or the probe or the transfer of materials from one to the other, or the welding of the probe to the cannula.

In a preferred embodiment the handle 62 of cannula 26 is molded about the arcuate tubular body 60. The handle 62 is made of FDA approved "T" grade ABS. The handle 62 is Y shaped in cross-sectioned and includes first and second leg 70 and 72. Handle 62 and first and second leg 70 and 72 are used to properly position the cannula in the subject. The handle 62 allows for the fingers of the surgeon using the cannula 26 to engage with the first and second leg 70, 72 making the cannula highly responsive to the surgeon's fingers. Extending from the handle 62 and adjacent the back end 68 of body 60 are first and second tabs 74, 76. These tabs 74, 76 are used to secure the dilator 28 and the seal nut 30 to the curved cannula 26 as will be described more fully hereinbelow. As can be seen in FIG. 5, the curved cannula further includes a stop 78 which has a body 80 and a thumbscrew 82 so as to allow the stop 78 to be selectively secured along any position on the body 60 of the curved cannula 26. The stop 78 is positioned adjacent the skin of the subject to which the cannula is inserted in order to maintain the position of the cannula relative to the subject as will be described below.

The cannula 26 is of sufficient rigidity such that the insertion of the probe 22 through the cannula 26 causes the probe 22 to bend without substantially deforming the curve of the cannula 26. It is to be understood that in a preferred embodiment, the cannula 26 will receive a probe which has an outer diameter of two millimeters.

Figure 6:
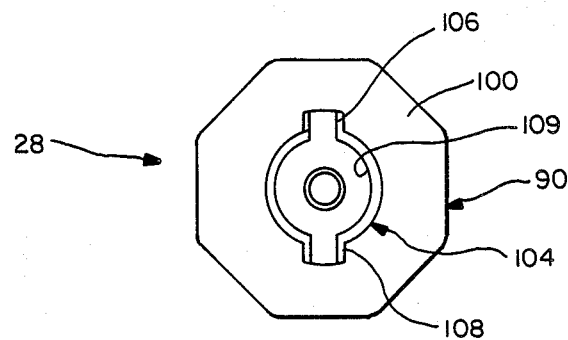
FIG. 6 is an end view of an embodiment of a dilator of the invention.
Figure 7:
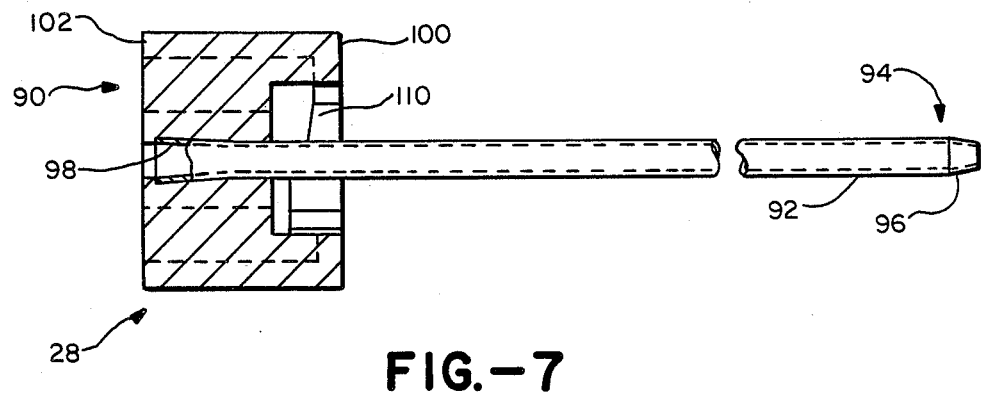
FIG. 7 is a partially sectioned side view of the dilator of FIG. 6.
Figure 8:
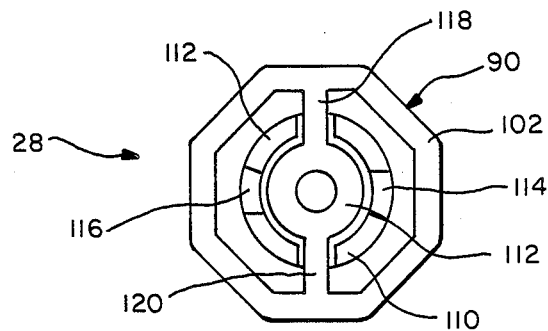
FIG. 8 is the other end view of the dilator of FIGS. 6 and 7.

The dilator of the invention is depicted in FIGS. 6, 7 and 8. The dilator 28 includes a handle 90 and an elongated tubular body 92 which extends from the handle 90. The insertion end 94 of the elongated tubular body 92 is provided in the shape of a truncated cone 96 which extends as can be seen in FIG. 9 from the curved cannula 26 when the body 92 of dilator 28 is disposed through the body 60 of the curved cannula 26.

As can be seen in FIG. 9, the flexible trocar 24 is positioned through the elongated tubular body 92 of dilator 28. In a preferred embodiment the elongated tubular body 92 is made of stainless steel.

The handle 90 in a preferred embodiment is molded about the slightly flaired back end 98 of the elongated tubular body 92. The handle 90 includes a front end 100 and a back end 102. The elongated tubular body 92 extends from the front end 100 as can be seen in FIG. 7. The front end 100 defines an aperture 104 positioned about the elongated tubular body 92. The aperture 104 is shaped to receive the back end 68 including the tabs 74, 76 of the curved cannula 26 for lockingly securing the curved cannula 26 to the dilator 28. The tabs 74, 76 are specifically received by rectangular portions 106 and 108 of aperture 104. With a twisting motion, the tabs are locked under aperture 104 such that the more restrictive diameter 109 of aperture 104 prevents the tabs and thus the curved cannula 26 from being removed from the handle 90 of the dilator 28. The tabs 74, 76 are further locked into position as they are urged by ramps 110, 112 up against stops 114 and 116 and against the front end 100. It is to be understood that other methods of providing a quick-release connection between the dilator 28 and cannula 24 are within the spirit of the invention. As can be seen in FIG. 8, the elongated tubular body 92 is held in position relative, to the handle 90 by web members 118, 120 and the casing 122 which is formed about the elongated tubular body 92.

FIG. 9 shows the assembly of the flexible trocar 24, the curved cannula 26 and the dilator 28 extending from the curved cannula 26. The dilator handle 90 is lockingly secured to the handle 62 of the curved cannula 26. In a preferred embodiment the dilator extends approximately two millimeters beyond the cannula with the dilator and cannula locked together. The trocar 24 is inserted into a subject 128.

Figure 10:
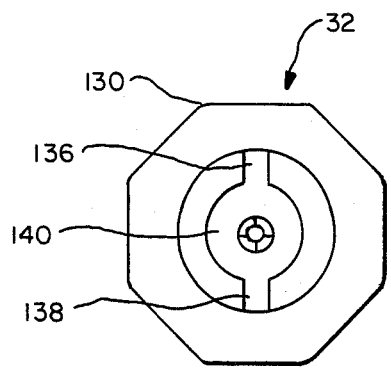
FIG. 10 is an end view of an embodiment of a trephine of the invention.
Figure 12:
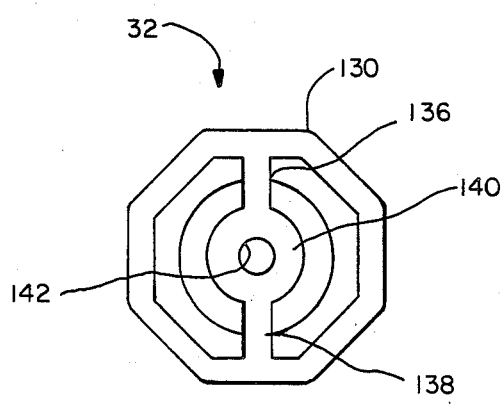
FIG. 12 is the other end view of the trephine of FIGS. 10 and 11.

A trephine 32 of the introduction set 20 is depicted in FIGS. 10, 11 and 12. Trephine 32 is essentially a hole saw for cutting a hole in fibrous tissue such as for example the annulus surrounding the softer nucleus tissue of the disc position between two vertebrae of a human back. The trephine 32 includes a handle 130 which is molded about a elongated tubular body 132. The tubular body 132 is comprised in a preferred embodiment of 304 stainless steel. Further the handle 130 as well as a handle 90 of the dilator 28, is comprised of the same material as is handle 62 of the curved cannula 26. The body 132 of the trephine 32 has at the insertion end 133 a plurality of teeth 134 that can saw through appropriate tissue, such as the annulus of a human back disc, as the handle 130 is rotated. In a preferred embodiment the teeth 134 are ground such that said teeth 134 taper inwardly. With this configuration the teeth 134 do not abrade the friction reducing lining 64 of the cannula 24. The handle 130 includes webs 136, 138 which secure a casing 140 which is molded about the back end 142 of the tubular body 132.

Once the cannula 26 is in the proper position, the dilator 28 can be removed and the trephine 32 can be inserted over the trocar 24 and through the tubular body 60 of the curved cannula 26. The trephine extends from the tubular body 60 past insertion end 66 of curved cannula 26 in order to saw through any fibrous tissue.

The seal nut 30 of the invention is depicted in FIGS. 13, 14, 15 and 16. Seal nut 30 includes a body 150 which retains an O-ring 152 (which is depicted only in FIGS. 15, 16 and 16a). In a preferred embodiment, the body 150 is comprised of the same material as for example the body of the curved cannula 26. The O-ring is comprised of 263-70 white FDA nitrile, in a preferred embodiment. As can be seen in FIG. 15, 16 and 16a O-ring 152 has a flat and squat profile in order to be properly retained by the seal nut 30 and in order to provide a tight seal about the probe 22 as probe 22 is inserted through internal diameter 153. Seal nut 30 includes a front end 154 and a back end 156. The front end 154 defines an aperture 158 which is similar in size and function as aperture 104 of the dilator 28. Aperture 158 includes first and second rectangular portion 160, 162 which act and function similar to the two rectangular portions 106 and 108 of the dilator 28.

The body 150 further includes ramps 164, 166 which act and function similarly to ramps 110 and 112 of the dilator 28. Stops 168, 170 act and function similarly to stops 114 and 116. Body 150 further includes collars 172, 174 and steps 173, 175 which are used to retain the O-ring 150 in position in the seal nut 30. As can be seen in FIG. 17, with the seal nut 30 locked in position against the back end of the handle 52 of the curved cannula 26, the O-ring 152 provides a seal against the back end 68 and thus with the space defined inside the tubular body 60 and tubular lining 64. The probe 22 has an elongated projection 180 which can be inserted through the tubular lining 64. The elongated projection 180 comes in sliding and sealing contact with the internal diameter 153 of the O-ring 152. Thus the seal nut 30, in a preferred embodiment, provides a vacuum seal between the tubular body 64 and the probe 24 with the O-ring 152.

Industrial Applicability

The operation of the introduction set 20 of the invention is as follows.

It is to be understood that the following description of the industrial applicability is drawn with respect to removal of herniated nucleus tissue from the disc between two vertebrae in the back of a human. It is also to be understood that other procedures can be performed with inventions which do not include the removal of such material using the probe 22.

The procedure for using the present invention is first to insert the trocar 24 percutaneously through the body 128 toward and intersecting the herniated disc. The insertion of the trocar 24 is monitored with a fluoroscope or other x-ray machine to insure that it is properly positioned in the disc. Once this is accomplished the cannula 26 with the tapered dilator 28 lockingly secured thereto is inserted over the trocar 24. The cannula 26 and dilator 28 are inserted into the subject 128 until they reach the outer annulus of the disc. It is to be understood that the trocar 24 and curved cannula 26 are especially useful for reaching the discs located between the L5-S1 vertebrae which is difficult to reach, if not impossible, with a straight cannula. Once it is confirmed with an x-ray that the dilator has reached the outer wall of the annulus the dilator is removed leaving the trocar and cannula in place.

The trocar 24 is of sufficient length such that with the cannula 26 fully disposed about the trocar 24, the back end 44 of the trocar 24 sticks out from the back end 68 of the cannula 26 prior to the cannula 26 being urged into the subject 128. This is to insure that the position of the trocar 24 is observable and can be maintained such that the trocar 24 is not accidentally urged further into the subject 128 as the cannula 26 is urged into the subject 128.

In practice the trocar 24 can be held by the back end 44 extending from the cannula 26 to insure that the trocar 24 is not further urged into the subject 128 with the urging of the cannula 26 into the subject 128. As the trocar 24 is flexible, the trocar 24 can be bent out of the way of the fluoroscope as the fluoroscope is positioned and repositioned in order to take the appropriate images. Without the capability of being bent, the trocar 24 would have be much shorter and would not be able to extend from the back end 44 of the cannula 26 prior to the insertion of the cannula 26 into the subject. Thus it is possible that the insertion of the curved cannula 26 into the subject 128 could cause a straight trocar to be further inserted into the subject 128 into undesirable locations.

After the cannula 26 is positioned the dilator 28 is then removed with the flexible trocar 24 left in place. Due to the length of the trocar 24 the position of the trocar can be observed and maintained during the removal of the dilator 28.

With the dilator 28 removed, the trephine 32 is placed over the trocar 24 and through the cannula 26. The annulus can be incised by turning the trephine 32 in clockwise motion. In a preferred embodiment a two millimeter hole is thus provided through the fibrous annulus. The trephine 32 and trocar 24 then are removed leaving the cannula 26 in place with the cannula stop 78 against the subject 128 to insure that the cannula position is maintained. Next the probe 22 with the seal nut 30 disposed about the probe 22 is inserted through the cannula 26 and the seal nut 30 is locked in place as described above. If desired a silicone lubricant can be applied to probe 22 prior to insertion into cannula 26 to further reduce friction. The probe 22 is urged completely through the cannula 26 and out the front insertion end 66 and finally through the hole drilled in the annulus and into the softer nucleus tissue. This is confirmed with appropriate x-rays. As described in the above identified U.S. Patent, the probe is then activated in order to cut and remove the herniated nucleus tissue. The probe 22 can be inserted further into the disc to remove more tissue along the path of the travel of the probe. Further it is possible to twist the cannula 26, by twisting the handle 62 in both a clockwise and counterclockwise manner in order to increase the number of paths which the probe 22 can follow if it is desired that still more tissue be removed from the herniated disc. Once this procedure is completed, the probe 22 is removed with the cannula 26 from the body 128.

From the above it can be seen that the introduction set 20 of the invention allows for the accurate placement of for example, probe 22 relative to a desired site on the subject 128. The curved cannula 26 provides for reaching sites which would otherwise be unreachable with a straight cannula. The flexible trocar 24 accommodates the curved cannula 26 and allows for displacement of at least part of the trocar 24 in order to accommodate other equipment such as x-ray machines and the like which must be positioned relatively close to the subject 128 in order to take an appropriate image of the area where work is to be performed.

It is to be understood that other uses may be made of the introduction set 20 other than with a probe such as probe 22. For example the introduction set 20 may be used to drain a cavity or to insert diagnostic or test instrumentation as well as insert other types of cutting probes for purposes of obtaining biopsies.

Other objects and advantages of the invention can be obtained from a review of the figures and the claims.

It is to be understood that other embodiments of the present invention can be provided and still come within the spirit and scope of the invention.

We claim:

1. A trocar for guiding the placement of a cannula relative to a desired site comprising:
   an elongate substantially flexible body of one piece, solid core construction;
   said body having a first flexible elongate section with a sharpened insertion end and a first selected diameter;
   said body having a second flexible elongate section with a second selected diameter that is substantially less than the first selected diameter, the flexibility of the said second flexible section being substantially greater than the flexibility of first flexible section; and
   coiled wire placed about and in contact with said second flexible section, said coiled wire for insuring the continued flexibility of said second flexible section.

2. The trocar of claim 1 wherein:
   said second flexible section has sufficient flexibility such that said second flexible section can be flexed by at least about ninety degrees.

3. The trocar of claim 1 wherein:
   said second flexible section has a first intersecting end with said first flexible section and second distal end; and
   wherein said coiled wire is secured to said first intersecting end and to said second distal end.

4. The trocar of claim 1 wherein the diameter of the coiled wire placed about the second flexible section is substantially the same as the diameter of the first flexible section.

5. The trocar of claim 1 wherein said distal end of said second flexible section is welded to said coiled wire to substantially form a hemisphere with a diameter substantially the same as said diameter of said first flexible section.

6. A medical instrument for guiding the placement of other medical instruments relative to a desired site comprising:
   an elongate substantially flexible body of one piece, solid core construction;
   said body having a first flexible elongate section with a sharpened insertion end and a first selected diameter;
   said body having a second flexible elongate section with a second selected diameter that is substantially less than the first selected diameter, the flexibility of said second flexible section being substantially greater than the flexibility of the first flexible section; and
   coiled wire placed about and in contact with second flexible section, said coiled wire for insuring the continued flexibility of said second flexible section.

7. The instrument of claim 6 wherein:
   said second flexible section has sufficient flexibility such that said second flexible section can be flexed by at least about ninety degrees.

8. The instrument of claim 6 wherein:
   said second flexible section has a first intersecting end with said first flexible section and a second distal end; and
   wherein said coiled wire is secured to said first intersecting end and said second distal end.

9. The instrument of claim 6 wherein the diameter of the coiled wire placed about the second flexible section is substantially the same as the diameter of the first flexible section.

10. The instrument of claim 8 wherein said distal end of said second flexible section is welded to said coiled wire to substantially form a hemisphere with a diameter substantially the same as the said diameter of said first flexible section.

11. In an introduction set having a curved cannula with a substantially rigid elongate arcuate tubular body, adapted for positioning a probe relative to a desired site in a subject, the invention comprising:
    an elongate flexible trocar means adapted for insertion into a subject relative to a desired site, said trocar having an insertion end and a back end,
    said flexible trocar having a flexible section, located adjacent the back end, adapted for extension from a subject;
    an elongate friction reducing tubular lining disposed inside of the tubular body of the curved cannula adapted for receiving a probe and reducing the friction encountered as a probe is received inside said cannula; and
    wherein the curved cannula is shorter than said trocar such that with the trocar extending from a subject, the tubular body of the cannula and said tubular lining can be threaded over the trocar and directed toward a subject and with the trocar extending from the back end of the cannula so that the trocar is observable prior to the insertion of the cannula into a subject and so that the position of said trocar can be maintained as the curved cannula is inserted into a subject.

12. The introduction set of claim 1 wherein said flexible section of said trocar which is adapted for extension from the subject has sufficient flexibility such that said second flexible section can be flexed by at least about ninety degrees.

13. The apparatus of claim 11 including:
    a trephine with cutting teeth which is insertable through the curved cannula; and
    said cutting teeth being tapered inwardly so as not to abrade the friction reducing tubular lining.

14. In the apparatus of claim 11 provided additionally with a seal nut with an O-ring secured in the seal nut adapted for providing a seal between the curved cannula and a probe, the invention comprising:
    the O-ring having a squat cross-section adapted for insuring a proper seal between the seal nut and the probe.

15. The apparatus of claim 11 including:
    a dilator means for easing the introduction of the curved cannula into a body;

said dilator means including a tubular body which is disposable through the tubular body of the cannula and which has an insertion end and a back end;

said dilator means including a conical means located at the insertion end of the dilator means and extendable from the cannula and adapted for expanding tissue of the subject;

said dilator means including a securing means, located at the back end of the dilator means, for lockingly securing said dilator means to the cannula.

16. A method for directing a probe to a hard to reach and desired site in a subject including the steps of:

introducing a flexible trocar into the subject, directed at the desired site;

providing a substantially rigid, curved cannula having a substantially rigid, elongate arcuate tubular body with first and second ends and having an elongate friction reducing tubular lining secured inside of the tubular body of the curved cannula, wherein the cannula is shorter than the trocar;

threading the first end of the curved cannula over the trocar until the trocar extends from the second end of the curved cannula;

introducing the curved cannula into the subject, directed at the desired site, while substantially maintaining the position of the trocar such that the trocar does not advance as the curved cannula is introduced;

removing the trocar through the cannula;

inserting the probe through the curved cannula, the cannula causing the probe to be conformed to the shape of the cannula and the lining easing the probe insertion step by reducing the friction between the probe and the cannula.

17. The method of claim 16 including the step of:

using a dilator to ease the introduction of the curved cannula into the subject.

18. The method of claim 16 including the step of:

providing a seal nut with an O-ring having a squat cross-section for ensuring a seal between the cannula and the probe as the probe is inserted through the O-ring and seal nut into the cannula.

19. The method of claim 16 including the step of:

inserting an instrument with cutting teeth that are tapered inwardly, prior to the insertion of the probe, in order to remove tissue ahead of the use of the probe to remove tissue.

20. In a curved cannula having a substantially rigid, elongate arcuate tubular body and provided additionally with a seal nut with an O-ring secured therein for providing a seal between the curved cannula and a probe, the invention comprising:

an elongate friction reducing tubular lining disposed inside of the tubular body of the curved cannula;

means for securing the tubular lining inside of the tubular body; and the O-ring having a squat cross-section adapted for insuring a proper seal between the seal nut and a probe.

21. In a curved cannula having a substantially rigid, elongate arcuate tubular body having a first end and a second end, the invention comprising:

an elongate friction reducing tubular lining disposed inside of the tubular body of the curved cannula;

means for securing the tubular lining inside of the tubular body;

wherein said tubular lining extends from about the first end of the tubular body to about the second end of the tubular body and has a first diameter; and wherein said securing means includes the first and second ends of the tubular body having second and third diameters that are less than the first diameter of the tubular lining.

* * * * *

UNITED STATES PATENT AND TRADEMARK OFFICE
CERTIFICATE OF CORRECTION

PATENT NO. : 4,863,430

DATED : September 5, 1989

INVENTOR(S) : Henry Klyce, et al.

It is certified that error appears in the above-identified patent and that said Letters Patent is hereby corrected as shown below:

On the title page:

Inventor: --Henry Klyce, Piedmont; Benjamin S. Clawson, Oakland, both of Calif.; Gary Onik, Wexford, PA; and Philip M. Chernack, West Hampstad, N.Y.--

Signed and Sealed this

Twenty-eighth Day of January, 1992

Attest:

HARRY F. MANBECK, JR.

Attesting Officer     Commissioner of Patents and Trademarks